US012703836B2

(12) United States Patent
González Canavaciolo et al.

(10) Patent No.: US 12,703,836 B2
(45) Date of Patent: Aug. 11, 2026

(54) **MIXTURE OF COMPOUNDS WITH HIGH MOLECULAR WEIGHTS, OBTAINED FROM SUGAR CANE WAX (*SACCHARUM OFFICINARUM* L.)**

(71) Applicant: CENTRO NACIONAL DE INVESTIGACIONES CIENTÍFICAS, Havana (CU)

(72) Inventors: Víctor Luis González Canavaciolo, Havana (CU); Roxana Vicente Murillo, Havana (CU); Laura Salahange González, Havana (CU); Vivian Molina Cuevas, Havana (CU); Sarahí Mendoza Castaño, Havana (CU)

(73) Assignee: CENTRO NACIONAL DE INVESTIGACIONES CIENTÍFICAS, Havana (CU)

( * ) Notice: Subject to any disclaimer, the term of this patent is extended or adjusted under 35 U.S.C. 154(b) by 332 days.

(21) Appl. No.: 18/576,577

(22) PCT Filed: May 23, 2022

(86) PCT No.: PCT/CU2022/050005
§ 371 (c)(1),
(2) Date: Jan. 4, 2024

(87) PCT Pub. No.: WO2023/284902
PCT Pub. Date: Jan. 19, 2023

(65) Prior Publication Data

US 2024/0327748 A1 Oct. 3, 2024

(30) Foreign Application Priority Data

Jul. 13, 2021 (CU) .................................. 2021-0060

(51) Int. Cl.

| | |
|---|---|
| ***A61K 36/00*** | (2006.01) |
| ***A61K 9/20*** | (2006.01) |
| ***A61K 9/28*** | (2006.01) |
| ***A61K 36/899*** | (2006.01) |
| ***A61P 25/28*** | (2006.01) |
| ***A61P 39/06*** | (2006.01) |
| ***C11B 1/10*** | (2006.01) |

(52) U.S. Cl.
CPC ............ *C11B 1/104* (2013.01); *A61K 9/2054* (2013.01); *A61K 9/2813* (2013.01); *A61K 9/2866* (2013.01); *A61K 36/899* (2013.01); *A61P 25/28* (2018.01); *A61P 39/06* (2018.01)

(58) Field of Classification Search
CPC ..................................................... A61K 36/89
See application file for complete search history.

(56) References Cited

U.S. PATENT DOCUMENTS

| | | | |
|---|---|---|---|
| 6,225,354 | B1 | 5/2001 | Perez |
| 2002/0058705 | A1 | 5/2002 | Gonzales et al. |
| 2004/0076732 | A1 | 4/2004 | Valix |
| 2006/0013842 | A1 | 1/2006 | Matkin et al. |
| 2011/0124894 | A1 | 5/2011 | Almagro |

FOREIGN PATENT DOCUMENTS

| | | | |
|---|---|---|---|
| EP | 0488928 | A2 | 8/1999 |

OTHER PUBLICATIONS

International Search Report in PCT/CU2022/050005, issued on Oct. 14, 2022, by the Spanish Patent and Trademark Office as International Searching Authority (5 pages).
Written Opinion in PCT/CU2022/050005, issued on Oct. 14, 2022, by the Spanish Patent and Trademark Office as International Searching Authority (5 pages).

*Primary Examiner* — Qiuwen Mi
(74) *Attorney, Agent, or Firm* — Koenig IP Works, PLLC; Katherine Koenig

(57) ABSTRACT

A mixture of compounds with high molecular weights is revealed, which presents neuroprotective effects, by inhibiting neurological deficit, which leads to an improvement in clinical symptoms, a significant reduction in neuronal death and therefore mortality. In addition, it has antioxidant effects that contribute to supporting its neuroprotective efficacy. Compositions for oral dosage, with said mixture of compounds as an active ingredient, are also disclosed, which can be used as nutritional or pharmaceutical compositions for the management of medical conditions related to the central nervous system, particularly neurodegenerative diseases that involve neuronal deterioration and death. The substances that make up this new active ingredient are fatty acids between 26 and 36 carbon atoms in the form of alkaline or alkaline earth salts, fatty alcohols between 24 and 34 carbon atoms and high molecular weight aldehydes, extracted and purified from sugar cane (*Saccharum officinarum* L.) wax. The combination of these three groups of high molecular weight substances, in the specific proportion revealed by the present invention, allows a synergistic effect to occur, which guarantees the desired pharmacological effect.

10 Claims, No Drawings

MIXTURE OF COMPOUNDS WITH HIGH MOLECULAR WEIGHTS, OBTAINED FROM SUGAR CANE WAX (*SACCHARUM OFFICINARUM* L.)

CROSS-REFERENCE TO RELATED APPLICATIONS

This Application is a U.S. National Phase Entry under 35 U.S.C. § 371 of and claims priority to International App. No. PCT/CU2022/050005, filed May 23, 2022, entitled MIXTURE OF COMPOUNDS WITH HIGH MOLECULAR WEIGHTS, OBTAINED FROM SUGAR CANE WAX (*SACCHARUM OFFICINARUM* L.), which claims priority to CU App. No. CU 2021-0060, filed Jul. 13, 2021, the entirety of both of which is incorporated herein by reference.

SUMMARY

Technical Sector

This invention is related to the food and pharmaceutical industries, by presenting a mixture of High Molecular Weight Substances (HMWS) with antioxidant and neuroprotective effects, which can be used as an Active Ingredient (AI) of nutritional supplements or pharmaceutical formulations. Said AI contains salts of fatty acids, fatty alcohols and high molecular weight aldehydes, obtained and purified from sugar cane wax (*Saccharum officinarum* L.), in specific proportions that guarantee a synergistic effect, where the pharmacological effect of the mixture described in the present invention is superior to the sum of the pharmacological effects of the groups of compounds that compose it.

Several diseases related to the nervous system affect the quality of life and can lead to the death of patients, so the need for new, safe and effective neuroprotective therapeutic strategies is a current problem. Among the many diseases in which the cells of the nervous system are affected we find spinal muscular atrophy, primary lateral sclerosis, progressive spinobulbar muscular atrophy and amyotrophic lateral sclerosis. The latter being the best known and most dangerous neurodegenerative disease as it has a fatal prognosis. This condition, widely known in the popular sphere for having led to the death of famous personalities such as the scientist Stephen Hawking, and the athletes Lou Gehrig, Gianluca Signorini and Stefano Borgonov, is characterized by the gradual loss of function and eventual death of the neurons responsible for muscle movement, which leads to progressive muscle paralysis.

Taking into account that neurological disorders affect the quality of life and some can cause the death of patients, constituting important health problems on a global scale, as well as the fact that existing conventional therapies fail to cure them or prevent their progression to the desired extent, it is necessary to search for new effective neuroprotective agents for the prevention and treatment of these medical conditions.

On the other hand, the search for antioxidant substances is also a current topic. The generation of reactive oxygen species and free radicals normally occurs during cellular metabolism, and under normal physiological conditions it is compensated by an antioxidant system that maintains the oxidation-reduction balance and cell survival. Nevertheless, there are several factors, such as exposure to pollutants and the environment, lifestyle and various pathologies, that can alter this balance, generating an excess and accumulation of free radicals, which causes Oxidative Stress (OE) (Poljsak, 2011). It has been shown that OE plays an important role in the development and progression of various chronic-degenerative pathologies such as atherosclerosis, cancer, heart disease and neurovegetative disorders (Maldonado 2010, Farlane 2004, Guichardant 2009). Therefore, consumption of antioxidant substances can prevent or reduce the cellular and functional deterioration of the organism generated by OE, exerting an additional benefit on the prevention of said pathologies (Oxilia 2010).

Previous Technique

There are several patents and publications on obtaining extracts from sugar cane wax (*S. officinarum* L.), but in no case the preparation of a mixture, with neuroprotective and antioxidant effects, with the composition shown in the present invention has been presented. In most of the published works, what is presented is the obtaining of pure mixtures of alcohols for the treatment of conditions related to the lipid profile, platelet hyperaggregability and coronary conditions. With these same objectives, mixtures of alcohols and fatty acids (where fatty alcohols predominate), pure mixtures of fatty acids, as well as combinations of said substances with different drugs, have also been prepared, with the aim of enhancing the above-mentioned pharmacological effects.

Among the first works published on this topic, we find the obtaining of a mixture of fatty alcohols (>90%) through saponification of sugar cane wax and extraction with organic solvents, which is effective in the treatment of hypercholesterolemia, atherosclerotic complications such as platelet hyperaggregability, ischemia and thrombosis, while preventing gastric ulcers and improving male sexual activity (Laguna, U.S. Pat. No. 5,856,316). The important pharmacological effects demonstrated by said mixture motivated the obtaining, from this wax, of other mixtures with high contents of fatty alcohols for these same pharmaceutical purposes, both by similar methods of obtaining (Almagro, US20070295326A1, Ribeiro BRPI0702137A and Matkin, US20060013842 A1), as well as by other technologies, such as fluid extraction under supercritical conditions (Shintaku BRPI0701341A2), multiphase hydrolytic extraction (Somaiya 1058/MUM/2005) and the reaction of wax with hydrogen in the presence of a catalyst (Somaiya WO2010103549).

With the aim of achieving pharmaceutical products with hypocholesterolemic, cardioprotective and antiplatelet effects, other extracts and mixtures have also been obtained from sugar cane wax, such as the one presented by Gonzales and collaborators (U.S. Pat. No. 6,486,205 B2), which is formed by fatty acids between 26 and 36 carbon atoms; that presented by Kutney and Wessman (US20050234025), who propose the combination of at least one alcohol or fatty acid of this wax with sterols and/or derivatives of ascorbic acid (without specifying the proportion between these substances); and the one proposed by Matkin and collaborators (US20060013842), who propose a mixture with a minimum of 60% fatty alcohols, up to 40% fatty acids and optionally salicylic acid, which can also be obtained from other waxes, animals or plants. Similarly, from other natural waxes, such as beeswax, sorghum and millet, extracts with alcohols and other fatty substances have been obtained, to which the same pharmacological effects on the lipid profile mentioned above are attributed (Pérez EP1189605B1 and Hargrove et al. US20060127449).

Regarding the use of fatty acids in neuroprotective compositions, we found that Miller (US20110280852A1) proposed unsaturated fatty acids between 18 and 22 carbon atoms, activated as nitro or keto acids, while Paquin and Rusell (US20020128316 and US20090280199) proposed the use of triglycerides (or their free acids) and omega-3 fatty acids, respectively, mixed with other substances.

In no case, a neuroprotective and antioxidant composition, consisting of a mixture of fatty acids with more than 26 carbon atoms in the form of salts, in specific proportions, containing also fatty alcohols and aldehydes of high molecular weight in specific proportions, has ever been disclosed.

Technical Problem

As previously stated, although neurological disorders are important health problems that affect the quality of life and can lead to death, existing conventional therapies are unable to cure them or prevent their progression to the desired extent. That is why it is necessary to search for new effective neuroprotective agents for the prevention and treatment of these medical conditions. On the other hand, the search for antioxidant substances is also necessary and topical, since there are several factors that generate an excess and accumulation of free radicals, which affect the development and progression of various chronic-degenerative pathologies.

Solution to the Problem

As a possible solution to the current problem, a mixture of High Molecular Weight Substances (HMWS) with antioxidant and neuroprotective effects, which is the object of the present invention, is presented. This mixture can be used as an Active Ingredient (AI) of nutritional supplements or pharmaceutical formulations. Said AI contains salts of fatty acids, fatty alcohols and high molecular weight aldehydes, obtained and purified from sugar cane (*Saccharum officinarum* L.) wax, in specific proportions that guarantee a synergistic effect, where the pharmacological effect of the mixture described in the present invention is superior to the sum of the pharmacological effects of the groups of compounds that compose it.

BRIEF DESCRIPTION OF THE INVENTION

The AI presented as the object of this invention is characterized by containing the following groups of compounds in specific proportions: fatty acids (60-80% by weight), fatty alcohols (10-30% by weight) and high molecular weight aldehydes (10-30% by weight). The main components, which are fatty acids, are present in the composition as alkali or alkaline earth salts in the following proportion: C26:0 between 0.3 and 5%, C27:0 between 0.3 and 5%, C28:0 between 20.0 and 40.0%, C29:0 between 1.0 and 3.0%, C30:0 between 12.0 and 25.0%, C31:0 between 0.5 and 2.0%, C32:0 between 5.0 and 15.0%, C33:0 between 0.5 and 3.0%, C34:0 between 5.0 and 18.0%, C35:0 between 0.3 and 1.5%, and C36:0 between 1.0 and 8.0%. The primary aliphatic alcohols present in the mixture are homologous compounds between 24 and 34 carbon atoms, among which 1-octacosanol (C28) predominates, and among the aldehydes, $\alpha\beta$ unsaturated with more than 48 carbon atoms predominates. This new AI can be formulated for oral administration in solid form (tablets, capsules) or liquid (suspensions), for which it is mixed with excipients accepted by the pharmaceutical industry.

It should be noted that the proportion in which high molecular weight substances are found in the IA object of the present invention is not achieved naturally through simple extraction and purification processes, but is the result of mixing, in specific quantities, the extracted and purified fractions of each group of substances, depending on the purity with which each fraction has been obtained. In this way, the final composition, object of the present invention, is the result of a standardization process, in which the contents of each group of compounds are brought to the specific concentrations and proportions described in this document, which guarantee a synergistic action between its components and the desired pharmacological effects; as has been determined through pharmacological studies.

In this regard, the powerful pharmacological effects of the present composition are much superior to the effects of administering these three groups of substances separately, which can be seen in the Examples of Implementation and demonstrates the occurrence of a synergistic effect, not deducible from the state of the art. Thus, the AI object of this invention significantly exceeds the pharmacological effects as an antioxidant, both of the fatty acid extract and of the extracts of fatty alcohols and high molecular weight aldehydes, and presents powerful neuroprotective effects that are not observed for any of the three types of substances that make up this IA.

The procedure for obtaining the pharmaceutical composition object of the present invention is characterized by an initial step of hydrolysis of cane wax, raw or refined, with alkaline or alkaline earth hydroxides, followed by selective extraction processes of alcohols and aldehydes, and purification steps of the remaining salts, as well as of the alcohol and aldehyde fractions, using in all the aforementioned stages organic solvents, or $CO_2$ under supercritical conditions, with a final standardization of the contents of the three groups of substances to which specific proportions described, which guarantee the desired pharmacological effect.

Advantageous Effects

The advantages of this composition over other existing ones, also obtained from cane wax, are that it has greater effectiveness as an antioxidant and a neuroprotective effect that is not present in any of the preceding compositions. This invention has industrial application, the composition is novel, and has an inventive character, as it cannot be deduced from the state of the art that the mixture of three groups of substances, in the proportions and concentrations specified, shows a synergistic effect with the pharmacological benefits. previously described. The present invention is related to the food and pharmaceutical industries, since the composition obtained can be used as a nutritional supplement, due to its beneficial effects on oxidative stress and also as a medicine to prevent neurological diseases, and those related to oxidative stress disorders.

EXAMPLES OF IMPLEMENTATION

Example 1. Obtaining the Mixture of High Molecular Weight Substances (HMWS), with Neuroprotective and Antioxidant Effects One kg of raw cane wax was subjected to a basic hydrolysis process with potassium hydroxide, after which the saponified wax was subjected to extraction with $CO_2$ under supercritical conditions, and both the mixture of remaining salts and the alcohol and aldehydes fractions, extracted with $CO_2$, were subjected to purification steps with hexane and acetone. The fractions obtained were analyzed by gas chromatography and spectrophotometry to determine their contents of salts, alcohols and aldehydes, and were subsequently mixed in the required proportions to achieve the following proportion: 76% fatty acids as potassium salts, 13% alcohols fatty and 11% high molecular weight aldehydes; where the fatty acids were in the following proportion: C26:0 1.5%, C27:0 1.4%, C28:0 30.6%, C29:0 1.2%, C30:0 13.5%, C31:0 1.0%, C32:0 8.3%, C33:0 1.7%, C34:0 11.6%, C35:0 1.4%, and C36:0 3.8%.

Example 2. Obtaining the Mixture of High Molecular Weight Substances (HMWS), with Neuroprotective and Antioxidant Effects One kg of refined cane wax was subjected to a basic hydrolysis process with calcium hydroxide, after which the saponified wax was subjected to extraction with hot hexane, the organic fraction was cooled and the recrystallized solid was subjected to a process purification by successive washes with ethanol and acetone. Both the mixture of remaining salts and the extracted and purified fraction were analyzed by gas chromatography and spectrophotometry to determine their contents of salts, alcohols and aldehydes, and were subsequently mixed in the required proportions to achieve the following proportion: 70% fatty acids as calcium salts, 19% fatty alcohols and 110% high molecular weight aldehydes; where the fatty acids were in the following proportion: C26:0 1.2%, C27:0 1.1%, C28:0 26.3%, C29:0 1.1%, C30:0 15.3%, C31:0 0.7%, C32:0 6.9%, C33:0 1.5%, C34:0 11.4%, C35:0 1.0%, and C36:0 3.7%.

Example 3. Evaluation of the Neuroprotective and Antioxidant Effects in a Cerebral Ischemia Induction Model For the evaluation of the neuroprotective effect of the mixture of high molecular weight substances, the object of the present invention, an experimental model of global cerebral ischemia by occlusion and reperfusion of the carotid arteries was used. The composition of High Molecular Weight Substances (HMWS) obtained in example 1 was subjected to a preclinical test with animals, in which its pharmacological effect was compared with the effects of pure extracts of Fatty Acids in the form of Salts (AcGS), fatty alcohols (AlcG) and high molecular weight aldehydes (AldG), which were administered in the dose equivalent to the proportion in which each one is present in 200 mg/kg of the HMWS Active Ingredient. Furthermore, the effect of HMWS was compared with the effect of pure free fatty acid (AcGL) extract administered at equal doses.

Male Mongolian gerbils (60-80 g) were used, which were adapted for 7 days to laboratory conditions (temperature of 20 to 25° C., relative humidity of 60±5%, light/dark cycles of 12 hours) with free access to water and food. The different substances to be evaluated were prepared as suspensions in an acacia/water vehicle (1%).

Once the quarantine was over, the gerbils were distributed into 8 groups: a negative control that only received vehicle and cerebral ischemia (CI) was not induced and 7 groups with induced CI. One of the groups with induced CI was the positive control, treated only with the vehicle, and the other 6 groups with CI were treated with HMWS (200 mg/kg), AcGS (132 mg/kg), AlcG (40 mg/kg), AldG (28 mg/kg), AcGL (200 mg/kg), and with aspirin (60 mg/kg) as a reference substance. All treatments were administered orally through intragastric intubation (0.5 mL/70 g body weight) 1 hour prior to induction of ischemia. Global cerebral ischemia was induced by bilateral ischemia and reperfusion. To do this, the gerbils were anesthetized in a halothane atmosphere, an incision was made in the ventral midline of the neck and the two common carotid arteries were exposed. These arteries were isolated and separated by placing a black silk thread around them, and they were then allowed to recover from anesthesia for 30 min. At the end of this time, the silk thread was removed and a pressure clip was placed on each carotid to completely obstruct blood flow for 5 min. The clip was then removed to allow blood recirculation for 24 hours.

Evaluation of neurological function was performed 4 hours after ischemia/reperfusion (according to McGraw, 1977), as follows: 0: absence of symptoms; 1: curvature of the torso or bristling of the hair; 2: ptosis; 3: movement in circles (circling behavior); 4: rear legs extended and 5: convulsions. The locomotor activity of the gerbils was evaluated in the open field at 24 hours post-ischemia (according to Katsumata et al, 2006). To do this, each gerbil was placed in the center of a box measuring 60.5 cm long×30 cm high×46 cm wide with the bottom divided into 12 quadrants of 14.5 $cm^2$. For 6 minutes, the number of times the gerbils crossed the different quadrants with their front legs and the number of times they stopped or leaned was quantified.

Once the behavioral observation was completed, the gerbils were anesthetized in a halothane atmosphere and blood samples were taken from the vena cava, which were collected in plastic tubes and mixed with EDTA (10%). Their brains were immediately removed for histological analysis. The blood was centrifuged at 3000 rpm for 10 min to obtain plasma, where biochemical quantification of lipid peroxidation and protein oxidation was carried out. To determine lipid peroxidation, the formation of substances reactive to thiobarbituric acid (SRATB) was quantified (according to Ohkawa et al., 1979) in plasma, and was expressed as nmol malondialdehyde (MDA)/mg of protein.

To determine protein oxidation, sulfhydryl (SH) groups were determined (technique described by Miao-Lin Hu, 1994). An aliquot of 50 μL of plasma, 950 μL of 10 mM DTNB was taken. It was incubated for 20 min at room temperature. The absorbance of the supernatant was read at 412 nm. The blank was prepared with DTNB and the total SH groups were calculated using an absorptivity of 13,600 cm-'M-' and expressed in mmol. The protein concentration was determined by the modified Lowry method (Marxwelll, 1987).

For histological analysis, brains were fixed in 10% buffered formaldehyde, dehydrated, embedded in paraffin, and sections containing the hippocampus were stained with hematoxylin and eosin. Sections from each brain were evaluated by a light microscopy scoring system for determination of damage to the pyramidal cells of the CA1 area of the hippocampus with bilateral averages. This histopathological scoring system (based on the method used by Bartus et al., 1998) was: 0=normally colored, densely packed cells with rounded soma and a well-colored central nucleus; 1=some shrinkage and irregularity in cell shape, with a pale chromatolytic region surrounded by a peripheral ring of cytoplasm; 2=some apparent cell loss with areas of pyknotic cells; 3=moderate cell loss and pyknosis; 4=loss of Nissl substance, indicating marked depletion of neurons and only an occasional neuron among numerous microglia.

Results

Global cerebral ischemia, even for a short period of time, leads to selective neurodegeneration in vulnerable regions of the brain, for example, the Cortical Adjacent (AC) region of the hippocampus. Particularly, CA1 pyramidal neurons are among the cells most vulnerable to ischemia/reperfusion damage (Sharma, 2005 and Kirino, 2000). The model of global cerebral ischemia induced by bilateral ligation of the two common carotid arteries for 5 minutes and their reperfusion for 24 hours constitutes a useful model in the evaluation of substances with a potential beneficial effect in ischemic stroke (Ravinder, 2009). Neurological evaluation according to the McGraw clinical symptom score and the increase in locomotor activity measured in the open field test constitute indicators of histological damage to brain tissue (McGraw, 1977; Katsumata, 2006).

The results showed the presence of clinical symptoms and increased locomotion in the positive control animals, alterations antagonized by aspirin, which agrees with what was reported for this model and supports its validity in our experimental conditions. This study demonstrates that the HMWS composition (200 mg/kg) has the ability to significantly reduce clinical symptoms (91.6% inhibition) and hyperlocomotion (86.1% inhibition) induced by global cerebral ischemia in Mongolian gerbils. Treatment with each pure extract of the individual components of HMWS (AcGS, AlcG and AldG), produced moderate, but significant, reductions in the clinical symptom score (36.6, 21.6 and 11.6% inhibition, respectively) and hyperlocomotion (33.4, 21.7 and 11.1% inhibition, respectively), compared to the positive control group. The comparison of HMWS (200 mg/kg) with each pure extract of its individual components was significant, showing greater efficacy, and even being superior to the sum of the effects of the three extracts, which demonstrates a synergistic or potentiating effect between the 3 components when managed together in the AI HMWS. (Table 1)

On the other hand, administration with HMWS (200 mg/kg) also produced protection from clinical symptoms, significantly higher than that of the pure AcGL extract (200 mg/kg), demonstrating better neurological protection with the extract that combines the presence of fatty acids in the form of salts, fatty alcohols and fatty aldehydes. (Table 1)

TABLE 1

Effects on clinical symptom score and locomotor activity (open field) in Mongolian gerbils with global brain Ischemia/Reperfusion (I/R).

| Treatment | Dosage (mg/kg/day) | SC score | Inhibition (%) | Crosses (#) | Inhibition (%) |
|---|---|---|---|---|---|
| Negative control (Vehicle) | 0 | 0 ± 0*** | — | 250.8 ± 14.8** | — |
| Positive Control (Vehicle + I/R) | 0 | 3.00 ± 0.52 | — | 355.5 ± 12.4 | — |
| HMWS + I/R | 200 | 0.25 ± 0.12***ab | 91.6 | 265.3 ± 9.4**ab | 86.1 |
| AcGS + I/R | 132 | 1.90 ± 0.35** | 36.6 | 320.5 ± 13.5* | 33.4 |
| AlcG + I/R | 40 | 2.35 ± 0.25* | 21.6 | 332.7 ± 13.5* | 21.7 |
| AldG + I/R | 28 | 2.65 ± 0.40* | 11.6 | 343.8 ± 12.2* | 11.1 |
| AcGL + I/R | 200 | 1.85 ± 0.32** | 38.3 | 322.8 ± 15.1* | 31.2 |
| ASA + I/R | 60 | 0.40 ± 0.35** | 86.6 | 286.2 ± 15.2* | 66.2 |

Data as Mean ± SEM (standard error of the mean), SC: Clinical symptoms

*p < 0.05;

**p < 0.01;

***p < 0.001comparison with the positive control group at p < 0.05 compared with AcGS and AcGL;

bp < 0.001 comparison with AlcG and with AldG (Mann Whitney U)

Table 2 shows the results of the histological study. The brains of the negative controls showed no alterations, while all the brains of the positive controls showed disappearance and damage of numerous pyramidal cells in the CA1 region. Treatment with aspirin (60 mg/kg), the reference substance, moderately (32.4%) and significantly reduced the histological score of brain damage, which validates the results in our experimental conditions.

HMWS treatment (200 mg/kg) significantly reduced the histological score of brain damage (89.8% inhibition) induced by bilateral ischemia reperfusion in Mongolian gerbils. The individual pure extracts with AcGS (132 mg/kg), AlcG (40 mg/kg) and AldG (28 mg/kg) significantly reduced the histological score compared to the positive control. The comparison between HMWS and each of the extracts of its individual components showed greater efficacy not only with respect to each pure extract, but also greater than the sum of the three. This result agrees with what was observed regarding clinical symptoms and reinforces the criterion of synergism between the three components present in the AI HMWS.

Administration with HMWS (200 mg/kg) was also more effective than the pure AcGL extract (200 mg/kg) to protect against histological damage, which corroborates what was observed regarding clinical symptoms, corroborating better neurological protection with the extract, which combines the presence of fatty acids in the form of salts, fatty alcohols and fatty aldehydes. (Table 2)

TABLE 2

Effects on the histological score of brains of Mongolian gerbils with Ischemia/Reperfusion (I/R).

| Treatment | Dosage (mg/kg/day) | Histologic Score | Inhibition (%) |
|---|---|---|---|
| Negative Control (Vehicle) | 0 | 0.00 ± 0.00 *** | — |
| Positive Control (Vehicle + I/R) | 0 | 2.96 ± 0.07 | — |
| HMWS + I/R | 200 | 0.30 ± 0.09 ***ab | 89.8 |
| AcGS + I/R | 132 | 1.97 ± 0.06 ** | 33.4 |
| AlcG + I/R | 40 | 2.32 ± 0.06 * | 21.6 |
| AldG + I/R | 28 | 2.66 ± 0.05 * | 10.1 |

TABLE 2-continued

Effects on the histological score of brains of Mongolian gerbils with Ischemia/Reperfusion (I/R).

| Treatment | Dosage (mg/kg/day) | Histologic Score | Inhibition (%) |
|---|---|---|---|
| AcGL + I/R | 200 | 1.95 ± 0.07 ** | 34.1 |
| ASA + I/R | 60 | 2.00 ± 0.15 ** | 32.4 |

Data as Mean ± SEM (standard error of the mean)

* $p < 0.05$;

** $p < 0.01$;

*** $p < 0.001$ comparison with positive control at $p < 0.05$ compared with AcGS and AcGL;

bp < 0.001 comparison with AlcG and with AldG (Mann Whitney U)

On the other hand, the AcGL extract (200 mg/kg) also produced an antioxidant effect by significantly reducing the plasma values of MDA (40% inhibition) and SH groups (36% inhibition) compared to the positive control. However, the comparison of HMWS (200 mg/kg) with AcGL (200 mg/kg) showed a superior antioxidant efficacy of HMWS, which supports its greater neuro-protective efficacy, demonstrated both in clinical symptoms and in the score of histological brain damage.

Treatment with ASA (60 mg/kg) did not modify any of these oxidative variables, which corresponds to its action profile, since its neuro-protective efficacy is based on its anti-platelet activity and not on antioxidant effects.

TABLE 3

Effects on plasma concentrations of MDA and sulfhydryl groups of Mongolian gerbils with cerebral Ischemia/Reperfusion (I/R).

| Treatment | Dosage (mg/kg/dia) | MDA (nM/mgPt) | Inhibition (%) | SH (mmol) | Inhibition (%) |
|---|---|---|---|---|---|
| Negative Control (Vehicle) | 0 | 38.8 ± 3.01** | — | 0.40 ± 0.02** | — |
| Positive Control (Vehicle + I/R) | 0 | 72.16 ± 5.88 | — | 0.65 ± 0.03 | — |
| HMWS + I/R | 200 | 39.55 ± 1.55***ab | 97.7 | 0.45 ± 0.01***ab | 80 |
| AcGS + I/R | 132 | 58.3 ± 1.8** | 41.54 | 0.56 ± 0.02** | 36 |
| AlcG + I/R | 40 | 63.5 ± 2.3* | 25.9 | 0.59 ± 0.01* | 24 |
| AldG + I/R | 28 | 68.50 ± 3.42 | 11 | 0.62 ± 0.02 | 12 |
| AcGL + I/R | 200 | 58.8 ± 2.1** | 40.04 | 0.56 ± 0.02** | 36 |
| ASA + I/R | 60 | 72.30 ± 4.63 | 0.0 | 0.62 ± 0.03 | 12 |

Data as Mean ± SEM (standard error of the mean)

*$p < 0.05$;

***$p < 0.001$ comparison with positive control at $p < 0.05$ compared with AcGS and AcGL; bp < 0.001 comparison with AlcG and with AldG (Mann Whitney U)

The results of the study on the oxidative variables associated with the global cerebral ischemia process induced by ischemia and reperfusion in Mongolian gerbils are shown in Table 3. The ischemia and reperfusion process increased the plasma concentrations of MDA (indicator of lipid peroxidation) and sulfhydryl groups (indicator of protein oxidation) in the positive control group, compared to that of the healthy animals in the negative control group.

Oral administration with HMWS (200 mg/kg) significantly prevented the increase in plasma concentrations of MDA and SH groups (97.7 and 80% inhibition, respectively), compared to the positive control group. Individual pure extracts with AcGS (132 mg/kg) and AlcG (40 mg/kg) significantly reduced plasma concentrations of MDA (41.5 and 25.9% inhibition, respectively) and SH groups (80 and 36% inhibition, respectively), compared to the positive control. By the way, the pure extract with AldG (28 mg/kg) produced a slight reduction on MDA (11% inhibition) and SH groups (12% inhibition), without reaching statistical significance. The comparison between HMWS and each of the extracts of its individual components showed greater efficacy not only with respect to each pure extract, but also greater than the sum of the three. Therefore, we are in the presence of an antioxidant effect of this new HMWS substance, which protects both lipid and protein structures, whose effectiveness corresponds to a synergistic effect between its three components.

Example 4. Evaluation of the Neuroprotective Effect in a Spinal Cord Ischemia Induction Model The neuroprotective effect of the HMWS mixture, object of the present invention, was also investigated using an experimental model of induction of ischemia in the spinal cord. The composition obtained in example 2 was subjected to a preclinical test in which its pharmacological effect was compared with the effects of pure extracts of Fatty Acids in the form of Salts (AcGS), fatty alcohols (AlcG) and high molecular weight aldehydes (AldG), which were administered at doses equivalent to that of those respective substances in 200 mg/kg of the HMWS Active Ingredient. Furthermore, the effect of HMWS was compared with that of pure extract of free fatty acids (AcGL) administered at equal doses.

Male New Zealand rabbits (1.8-2.2 kg) were used, which were adapted for 15 days to laboratory conditions (temperature of 20 to 25° C., relative humidity of 60±5%, light/dark cycles of 12 hours), with free access to water and food.

The substances HMWS, AcGS, AlcG, AldG, AcGL and aspirin were prepared as suspensions in an acacia/water vehicle (1%). Once the quarantine was completed, the rabbits were distributed into 8 groups: a negative control that only received vehicle and was not induced ischemia and 7 groups with spinal cord ischemia: a positive control treated only with the vehicle, and 6 groups were treated with HMWS (200 mg/kg), AcGS (132 mg/kg), AlcG (40 mg/kg), AldG (28 mg/kg), AcGL (200 mg/kg), and aspirin (2 mg/kg) as reference substance. All treatments were administered orally via intragastric tubing (1 mL/2 kg body weight) for 10 days.

For the induction of ischemia in the spinal cord, the rabbits were anesthetized with thiopental (20 mg/kg i.v.). The abdomen was depilated, an antiseptic solution was applied, an incision was made in the ventral midline and the retroperitoneal space was penetrated. The aorta and left renal artery were dissected and exposed. The aorta was ligated by placing a clip immediately below the left renal artery for 20 minutes, after which it was removed and the reperfusion period began. The incision was sutured. At 4 and 24 hours of reperfusion, the neurological deficit of the animals was blindly evaluated by 2 independent observers (according to Zivin et al., 1982). The scale used was the following:

Grade 0: complete paralysis

Grade 1: partial neurological deficit

Grade 3: normal

The animals were sacrificed 24 hours after reperfusion. For histological analysis, marrow sections were extracted. Once the spinal cord (lumbar) segments were extracted, they were fixed in 10% buffered formaldehyde. Samples were dehydrated in alcohols of increasing concentrations, embedded in paraffin and cut into 4 μm sections on a horizontal micrometer. Sections were stained with hematoxylin and eosin. They were subsequently observed under an Olympus BH2 microscope. Spinal cord lesions were blindly evaluated using the criteria described by De Girolami, 1982 and Zivin, 1982.

3—No injuries

2—Mild: When only 1 to 10 necrotic neurons are detected in the gray matter sample with less than 33% of the substance involved.

1—Moderate: When only 10 to 20 necrotic neurons are detected in the gray matter sample with 33-66% of the section area involved.

0—Severe: When the gray matter sample is only detected to contain more than 20 necrotic neurons with more than 66% of the section area involved.

Results

Occlusion and reperfusion of the abdominal aorta produces neurological damage in the rabbit that results in paralysis of the hind legs and the inability to jump. Table 4 shows the score of the clinical symptoms of the neurological deficit, and the percentage of mortality. With 20 minutes of occlusion of the abdominal aorta, the positive control animals presented this symptomatology, with a score significantly lower than the negative control group (healthy animals), while also presenting 80% mortality. The administration of aspirin (2 mg/kg), the reference substance, significantly protected both clinical symptoms and mortality, which validates the results obtained in the experimental conditions. Treatments with repeated doses of HMWS (200 mg/kg) significantly increased the clinical symptom score at 4 and 24 hours of abdominal aortic reperfusion, and reduced overall mortality. Treatments with AcGS (132 mg/kg), AlcG (40 mg/kg) and AldG (28 mg/kg) significantly protected from clinical symptoms at 4 and 24 hours, while only AcGS reduced mortality by 50% compared to the positive control group (80%). The comparison of HMWS (200 mg/kg) with respect to the pure extracts of its individual components also showed statistical significance, indicating greater efficacy of HMWS than each one separately. Furthermore, the extract with AcGL (200 mg/kg) also protected against clinical symptoms and mortality, although its comparison with HMWS showed greater efficacy of the latter.

Therefore, the comparison between the results of the treatments showed greater effectiveness of HMWS compared to the others in improving clinical symptoms, 4 and 24 hours after reperfusion, as well as in reducing mortality. The HMWS composition significantly protected against mortality, such that the frequency of deaths in the group treated with this substance (0.0%) was significantly lower than that of the positive controls (80%), indicating 100% of protection.

The histological analysis (Table 5) showed severe lesions in the spinal cords of the animals in the positive control group, characterized by neuronal necrosis and vacuolization of the neuropil. Aspirin produced modest but significant protection relative to the positive control.

Treatment with HMWS (200 mg/kg) significantly inhibited histological damage in the spinal cord, caused by neurological deficit, achieving the highest efficacy of all the treatments applied (93.3% inhibition). Treatments with AcGS (132 mg/kg), AlcG (40 mg/kg), and AldG (28 mg/kg) moderately protected from histological damage (40, 24, and 11.6% inhibition, respectively), with efficacy being of the HMWS greater than that of each of them and even greater than the sum of the effects of the three. This result indicates the presence of a synergistic effect of the three substances present in the IA HMWS to protect from neurological deficit in the spinal cord of rabbits with ischemia and reperfusion. Furthermore, the protection of HMWS was higher than that observed with the pure AcGL extract, demonstrating advantages for this new AI.

In conclusion, treatment with the HMWS composition presented advantages, enhancing the neuroprotective benefit, effectively reducing clinical symptoms, mortality and the histological damage score in the spinal cord.

TABLE 4

Effects on symptomatology and mortality in rabbits with spinal cord damage induced by Ischemia/Reperfusion (I/R).

| Treatment | Dosage (mg/kg/day) | Score 4 h | Score 24 h | Mortality 24 h (%) |
|---|---|---|---|---|
| Negative Control (Vehicle) | 0 | 2 ± 0*** | 2 ± 0*** | 0 |
| Positive Control (Vehicle + I/R) | 0 | 0.30 ± 0.17 | 0.15 ± 0.1 | 80 |
| HMWS + I/R | 200 | 1.75 ± 0.3***ab | 1.5 ± 0.13***ab | 0++ c d |
| AcGS + I/R | 132 | 1.05 ± 0.26** | 0.82 ± 0.18** | 50+ |
| AlcG + I/R | 40 | 0.82 ± 0.18* | 0.72 ± 0.11* | 60 |
| AldG + I/R | 28 | 0.54 ± 0.16* | 0.48 ± 0.1* | 70 |

TABLE 4-continued

Effects on symptomatology and mortality in rabbits with spinal cord damage induced by Ischemia/Reperfusion (I/R).

| Treatment | Dosage (mg/kg/day) | Score 4 h | Score 24 h | Mortality 24 h (%) |
|---|---|---|---|---|
| AcGL + I/R | 200 | 1.1 ± 0.22** | 0.80 ± 0.15** | 50+ |
| ASA + I/R | 2 | 0.90 ± 0.25* | 0.50 ± 0.24* | 40+ |

Data as Mean ± SEM (standard error of the mean)
*p < 0.05;
**p < 0.01;
***p < 0.001 comparison with positive control at p < 0.05 compared with AcGS and AcGL;
bp < 0.001 comparison with AlcG and with AldG (Mann Whitney U)
+p < 0.05;
++p < 0.01; comparison with positive control
c p < 0.01 comparison with AcGS and AcGL;
d p < 0.05 comparison with AlcG and AldG
(Fisher exact probability test)

TABLE 5

Effects on the histological score of the spinal cord of rabbits with Ischemia/Reperfusion (I/R).

| Treatment | Dosage (mg/kg/day) | Histologic Score | Inhibition (%) |
|---|---|---|---|
| Negative Control (Vehicle) | 0 | 3.00 ± 0.00 *** | — |
| Positive Control (Vehicle + I/R) | 0 | 0.00 ± 0.05 | — |
| HMWS + I/R | 200 | 2.80 ± 0.19 ***ab | 93.3 |
| AcGS + I/R | 132 | 1.20 ± 0.14 ** | 40 |
| AlcG + I/R | 40 | 0.72 ± 0.13 * | 24 |
| AldG + I/R | 28 | 0.35 ± 0.08 * | 11.6 |
| AcGL + I/R | 200 | 1.22 ± 0.13 ** | 40.6 |
| ASA + I/R | 60 | 0.9 ± 0.15 * | 30 |

Data as Mean ± SEM (standard error of the mean)
* p < 0.05;
** p < 0.01;
*** p < 0.001 comparison with positive control at p < 0.05 compared with AcGS and AcGL;
bp < 0.001 comparison with AlcG and with AldG (Mann Whitney U)

Example 5. Evaluation of the Neuroprotective Effect in a Model of Neuronal Damage Induced with a Toxic Agent The neuroprotective effect of the HMWS mixture, object of the present invention, was also investigated using an experimental model of neuronal damage induced with kainic acid. The composition obtained in example 2 was subjected to a preclinical test in which its pharmacological effect was compared with the effects of pure extracts of Fatty Acids in the form of Salts (AcGS), fatty alcohols (AlcG) and high molecular weight aldehydes (AldG), prepared with doses equal to the doses of those respective substances in the HMWS Active Ingredient. In addition, it was compared with a pure extract of free Fatty Acids (AcGL).

Male Wistar rats (250-300 g) were used, which were adapted for 7 days to laboratory conditions (temperature of 20 to 25° C., relative humidity of 60±5%, light/dark cycles of 12 hours) with free access to water and food.

The substances HMWS, AcGL, AcGS, AlcG, AldG and aspirin were prepared as suspensions in an acacia/water vehicle (1%). Once the quarantine was over, the rats were distributed into 7 groups: a negative control without neuronal damage, since it only received vehicle, and 6 groups with neurotoxicity. Of the latter, one was a positive control treated only with the vehicle, and the other 5 groups were treated with HMWS (200 mg/kg), AcGS (132 mg/kg), AlcG (40 mg/kg), AldG (28 mg/kg) and AcGL (200 mg/kg). All treatments were administered orally through intragastric intubation (5 mL/kg body weight) 30 minutes prior to neurotoxic induction.

Neurotoxicity was induced by injection of kainic acid (6 mg/kg; i.p) to the rats. One hour later, the exploratory activity of the rats was evaluated in the open field (Fernández, 1987). To do this, the rats were placed in the center of a box (60.5 cm long×30 cm high×46 cm wide, bottom divided into 12 quadrants of 14.5 $cm^2$), and the number of times they crossed the different quadrants was quantified (C), as well as the times they stopped or leaned (P) during the 6 minutes following their placement in the device.

Once the behavioral experiment was completed, the rats were sacrificed in a halothane atmosphere, and the brains were quickly extracted and fixed in 10% buffered formaldehyde. Tangential brain sections were subsequently embedded in paraffin, cut, and stained with 1% acid fuchsin for 30 seconds for the detection of neuronal death (Lee, 2000). The presence of acidophilic neurons (positive for kainic acid) is a variable indicative of neuronal damage (Lee, 2002). To count kainic acid-positive cells, the pyramidal neurons of CA1 and CA3 of the hippocampus of each rat were studied in a light microscope in an area of 250 $\mu m^2$ in the center of these regions (Savaskan, 2002).

Results

Kainic acid is an analogue of glutamate, which when injected systemically or intracerebral produces neurotoxicity due to selective neuronal degeneration, in which the receptors for this substance participate (Coyle, 1983; Borg, 1991). Depending on the dose administered, kainic acid can induce non-convulsive or convulsive seizures, in such a way that non-convulsant doses induce changes in spontaneous behavior and damage the process related to the maintenance of attention, making it possible to analyze these effects on animal behavior (Mikulecka, 1999).

The administration of kainic acid induced a reduction in both components of exploratory activity (crossings and stops) and in global exploratory activity compared to the negative control group, which corresponds to the behavioral changes reported in the literature and confers validity to the model in our experimental conditions. The oral administration of single doses with HMWS (200 mg/kg) increased both components, as well as the total activity, compared to the positive control group, achieving the highest efficacy of all treatments. Treatments with AcGS (132 mg/kg), AlcG (40 mg/kg) and AldG (28 mg/kg) increased crossings and stops, as well as total activity, although the latter only reached statistical significance over the total. HMWS (200 mg/kg) was more effective than each of its individual components (AcGS, AlcG and AldG) on all the behavioral variables measured, and even higher than the sum of the effects of the three substances. Furthermore, the effectiveness of HMWS to increase crossings, stops and their summation was higher than that of the AcGL extract (200 mg/kg), which corroborates the advantage of this new AI. (Table 6)

Table 7 shows the results of the histological study. As expected, systemic administration of kainic acid produced neuronal loss, which is related to the effects that this excitotoxin induces in the rat hippocampus, by inducing the loss of pyramidal neurons in the hippocampal regions CA1 and CA3 (Mikulecka, 1999; Pérez, 1996). Administration with HMWS (200 mg/kg) significantly decreased the degree of neuronal death (85.3% inhibition). Pure extracts of AcGS (132 mg/kg), AlcG (40 mg/kg), and AldG (28 mg/kg) moderately reduced neuronal death (35, 22.05, and 11.7% inhibition, respectively). The comparison between the effects of HMWS with each of its individual components showed significant differences, indicating greater effectiveness of this extract that presents the three substances in combination. At the same time, its efficacy was greater than the sum of the individual effects of each substance separately, indicating the presence of a synergistic effect in the neuroprotection of HMWS in this model.

On the other hand, the AcGL extract (200 mg/kg) also exerted a neuroprotective effect by moderately protecting against neuronal death exerted by kainic acid (30.8% inhibition), although in this case the HMWS extract was also superior in efficacy.

Therefore, the fact that the HMWS composition protected against neuronal death in this model corroborates its neuroprotective effects, observed in the models described in the previous examples, and its superior efficacy to the rest of the treatments, as well as the synergistic effect between its components represent potential advantages in the treatment of neurodegenerative diseases.

TABLE 6

Effects on exploratory activity (open field) of rats with kainic acid (KA)-induced neurotoxicity.

| Treatment | Dosage (mg/kg/day) | Crosses (#) | Stops (#) | Crosses + Stops (#) |
|---|---|---|---|---|
| Negative Control (Vehicle) | 0 | 40.0 ± 3.83*** | 15.8 ± 1.88*** | 55.8 ± 3.41*** |
| Positive Control (Vehicle + KA) | 0 | 17.7 ± 4.56 | 4.3 ± 1.12 | 22.0 ± 3.2 |
| HMWS + KA | 200 | 38.7 ± 2.5**ab | 15.00 ± 1.9**ab | 53.7 ± 4.3**ab |
| AcGS + KA | 132 | 27.5 ± 2.3* | 10.3 ± 1.5* | 37.8 ± 3.5* |
| AlcG + KA | 40 | 24.0 ± 4.2* | 8.1 ± 0.9* | 32.1 ± 2.2* |
| AldG + KA | 28 | 21.8 ± 3.7 | 6.6 ± 1.1 | 28.4 ± 2.8* |
| AcGL + AA | 200 | 28.6 ± 3.4* | 10.2 ± 2.5* | 38.8 ± 4.5* |

Data as Mean ± SEM (standard error of the mean)
*p < 0.05;
**p < 0.01;
***p < 0.001 comparison with positive control at p < 0.05 compared with AcGS and AcGL;
bp < 0.001 comparison with AlcG and with AldG (Mann Whitney U)

TABLE 7

Effects on neuronal death in rats with kainic acid (KA) -induced neurotoxicity.

| Treatment | Dosage (mg/kg/day) | Neuronal death (#) | Inhibition (%) |
|---|---|---|---|
| Negative Control (Vehicle) | 0 | 0.00 ± 0.00 *** | — |
| Positive Control (Vehicle + KA) | 0 | 34.00 ± 1.25 | — |
| HMWS + KA | 200 | 5.0 ± 0.8 ***ab | 85.3 |
| AcGS + KA | 132 | 22.1 ± 1.5 * | 35 |
| AlcG + KA | 40 | 26.5 ± 1.2 * | 22.05 |
| AldG + KA | 28 | 30.0 ± 0.6 * | 11.7 |
| AcGL + KA | 200 | 23.5 ± 1.10 * | 30.8 |

Data as Mean ± SEM (standard error of the mean)
(# of cells positive for acid fuschina stain)
* p < 0.05;
** p < 0.01;
*** p < 0.001 comparison with positive control at p < 0.05 compared with AcGS and AcGL;
bp < 0.001 comparison with AlcG and with AldG (Mann Whitney U)

Example 7. Obtaining Tablets 5 kg of the composition obtained in example 1 were mixed with 5 kg of carboxymethylcellulose, 30 kg of lactose and 10 kg of microcrystalline cellulose in a rotating stainless steel drum at 5 rpm for 10 minutes. Subsequently, 1 kg of magnesium stearate was added to the previous mixture and the complete granules continued to be mixed in the rotating drum at 5 rpm for 5 minutes.

The final mixture was pressed with a tablet press at a speed of 30,000 tablets/hour to obtain tablets with an average weight of 450 mg. These had a round convex shape on both sides with a diameter of 12 mm, their disintegration time in water was less than 20 min, their friability was less than 1%, and their hardness was between 44 and 60 N, according to USP methods.

Example 8. Coating of Tablets

The tablets obtained in the previous example can be coated. To do this, they were mixed with the following ingredients in a propeller mixer to form a coating suspension: 25 kg of cellulose acetophthalate in a 28% aqueous solution, 0.6 kg of talc, 0.9 kg of titanium dioxide. The coated tablets had a final weight of 470 mg. Colorant can be added to the coating solution and the coated tablets can be polished with wax or paraffin.

Example 9. Obtaining Capsules

The granules obtained in Example 7 can be encapsulated alternatively. For this purpose, size 1 hard gelatin capsules were filled with 430 mg of the granules obtained in Example 7, thereby obtaining capsules with the following characteristics: average weight 455.0+/−30 mg, disintegration in water, less than 20 minutes.

Example 10. Preparation of Suspension 200 g of the composition presented in Example 2, 40 kg of sorbitol, 5.00 g of preservatives (mixture of methyl and propyl parabens dissolved in alcohol) were mixed with 158 liters of water in a stainless steel reactor provided with a stirring propeller. Subsequently, 2 kg of apple essence was added and stirring was continued. The suspension formed was packaged at a rate of 115 mL in amber glass bottles with plastic lids and one tablespoon (15 mL) was recommended as a dosage unit.

The invention claimed is:

1. A mixture of compounds with high molecular weights, obtained from sugar cane wax, characterized by being made up of fatty acids between 26 and 36 carbon atoms in a form of alkaline or alkaline earth salts, primary aliphatic alcohols between 24 and 34 carbon atoms and αβ unsaturated aldehydes with more than 48 carbon atoms.

2. The mixture of compounds with high molecular weights according to claim 1, characterized by containing between 60% and 80% by weight of fatty acids in the form of alkali or alkaline earth salts in the following proportion: C26:0 between 0.3 and 5%, C27:0 between 0.3 and 5%, C28:0 between 20.0 and 40.0%, C29:0 between 1.0 and 3.0%, C30:0 between 12.0 and 25.0%, C31:0 between 0.5 and 2.0%, C32:0 between 5.0 and 15.0%, C33:0 between 0.5 and 3.0%, C34:0 between 5.0 and 18,0%, C35:0 between 0.3 and 1.5%, and C36:0 between 1.0 and 8.0%; as well as homologous primary aliphatic alcohols, present in an amount of 10-30% by weight, between 24 and 34 carbon atoms, among which 1-octacosanol predominates; and aldehydes, present in an amount of 10-30% by weight, among which unsaturated αβ with more than 48 carbon atoms predominate.

3. The mixture of compounds with high molecular weights according to claim 1, characterized in that the compounds are obtained from raw or refined sugar cane wax through a process that involves saponification of the wax with alkaline or alkaline earth hydroxides, followed by successive stages of extraction and purification of fractions of salts of fatty acids, alcohols and high molecular weight aldehydes, with organic solvents or $CO_2$ fluids under supercritical conditions, followed by a final standardization of the concentrations of said compounds at the required concentrations.

4. The mixture of compounds with high molecular weights according to claim 1, characterized by their use in neuroprotective and antioxidant compositions.

5. A nutritional composition characterized by containing the mixture of high molecular weight compounds according to claim 1, in doses between 5 and 50 mg per dosage unit, as well as excipients.

6. The nutritional composition according to claim 5, in a form of tablets or capsules for oral use, which is characterized by containing, in addition to the mixture of high molecular weight compounds, filler excipients, adhesives, disintegrants, lubricants and colorants.

7. The nutritional composition according to claim 5, in a form of a suspension for oral use, which is characterized by containing, in addition to the mixture of high molecular weight compounds, suspending agents, preservatives, colorings, sweeteners, flavorings and solvents.

8. A pharmaceutical composition characterized by containing the mixture of high molecular weight compounds according to claim 1, in doses between 5 and 50 mg per dosage unit, as well as excipients accepted by the pharmaceutical industry.

9. The pharmaceutical composition according to claim 8, in a form of tablets or capsules for oral use, which is characterized by containing, in addition to the mixture of high molecular weight compounds, filler excipients, adhesives, disintegrants, lubricants and colorants.

10. The pharmaceutical composition according to claim 8, in a form of a suspension for oral use, which is characterized by containing, in addition to the mixture of high molecular weight compounds, suspending agents, preservatives, colorings, sweeteners, flavorings and solvents.

* * * * *